(12) United States Patent
Liu et al.

(10) Patent No.: US 7,968,319 B2
(45) Date of Patent: Jun. 28, 2011

(54) METHOD FOR PRODUCING 1,3-PROPANEDIOL AND 2,3-BUTANEDIOL FROM RAW STARCH MATERIAL

(75) Inventors: Dehua Liu, Beijing (CN); Keke Cheng, Beijing (CN); Hongjuan Liu, Beijing (CN); Rihui Lin, Beijing (CN); Jian Hao, Beijing (CN)

(73) Assignee: Tsinghua University, Beijing (CN)

( * ) Notice: Subject to any disclaimer, the term of this patent is extended or adjusted under 35 U.S.C. 154(b) by 460 days.

(21) Appl. No.: 11/917,682

(22) PCT Filed: Jun. 13, 2006

(86) PCT No.: PCT/CN2006/001291
§ 371 (c)(1),
(2), (4) Date: May 28, 2008

(87) PCT Pub. No.: WO2006/133637
PCT Pub. Date: Dec. 21, 2006

(65) Prior Publication Data
US 2009/0081745 A1 Mar. 26, 2009

(30) Foreign Application Priority Data
Jun. 17, 2005 (CN) .......................... 2005 1 0011959

(51) Int. Cl.
*C12P 7/18* (2006.01)
*C12P 39/00* (2006.01)
(52) U.S. Cl. .......................................... 435/158; 435/42
(58) Field of Classification Search .................. None
See application file for complete search history.

(56) References Cited

U.S. PATENT DOCUMENTS

| 5,254,467 | A | * | 10/1993 | Kretschmann et al. ....... 435/158 |
| 2003/0022323 | A1 | | 1/2003 | Dunn-Coleman et al. |
| 2003/0157674 | A1 | | 8/2003 | Emptage et al. |

FOREIGN PATENT DOCUMENTS

| CN | 1244586 A | 2/2000 |
| CN | 1324953 A | 12/2001 |
| CN | 1348007 A | 5/2002 |
| CN | 1357628 A | 7/2002 |
| CN | 1382219 A | 11/2002 |
| CN | 1570123 A | 1/2005 |
| CN | 1763210 A | 4/2006 |
| GB | 315263 A | 8/1930 |

OTHER PUBLICATIONS

Chi N. et al. 2003 "The Screening of the 1,3-PD High-Production Strain from Clostridiums and Studies on Its Fermentation medium" *Food and Fermentation Industries* 29: 10-13.
Liu Y. et al. 2002 "Production process of 1,3-Propanediol" *China Synthetic Fiber Industry* 25: 42-45.
Liu Z. et al. 2004 "Industrial Application and Production Process of 1,3-Propanediol" *Machining of Farm Product* No. 2:26-27.
Wang D. et al. 2000 "Production of 2,3-Butanediol in Fermentation" *Fine and Specific Chymist Product* 7:20-21.
Wu B. et al. 2004 "Fermentative Production of 1,3-Propanediol from Glycerol by *Clostridium Butyricum*" *Industrial Microbiology* 34: 21-25.
International Search Report for published international application (PCT/CN2006/001291), which lists references 1-16 above. Pub Date Sep. 21, 2006.

* cited by examiner

*Primary Examiner* — Herbert J. Lilling
(74) *Attorney, Agent, or Firm* — Knobbe Martens Olson & Bear LLP

(57) ABSTRACT

The invention discloses a method for producing 1,3-propanediol and 2,3-butanediol from raw starch materials, including the following steps: 1) *Candida krusei* or *Hansenula Arabitolgens* Fang are inoculated into a fermentation medium with the saccharifying liquid of the raw starches as a carbon source; the yeast cells are cultured on an aerobic condition until glucose-consuming-rate is significantly reduced, and then fermented anaerobically to a glucose concentration from 5 to 10 g/L; the fermentation broth is collected and filtered to remove the yeast cells in the broth, and the resultant filtrate is glycerin fermentation broth; 2) *Klebsiella*, *Clostridium butyricum*, or *Clostridium pasteurianum* are inoculated into a fermentation medium in which the glycerin fermentation broth obtained from step 1) serves as a carbon source; the bacteria are fermented anaerobically for 30-32 hours, and then fermented aerobically when the production rate of 1,3-propanediol decreased obviously, and the fermentation was stopped when the concentration of glycerin is reduced to a level below 10 g/L, and finally 1,3-propanediol and 2,3-butanediol are obtained. The method of the present invention can effectively reduce production cost and increase productivity.

15 Claims, No Drawings

METHOD FOR PRODUCING 1,3-PROPANEDIOL AND 2,3-BUTANEDIOL FROM RAW STARCH MATERIAL

RELATED APPLICATIONS

This application is a U.S. National Phase of International Application No. PCT/CN2006/001291, filed Jun. 13, 2006, designating the U.S. and published not in English on Dec. 21, 2006 as WO 2006/133637, which claims the benefit of Chinese application No. 200510011959.6, filed Jun. 17, 2005.

TECHNICAL FIELD

The present invention relates to a method for producing 1,3-propanediol and 2,3-butanediol, particularly a method for producing 1,3-propanediol and 2,3-butanediol from raw starch materials.

BACKGROUND ARTS 1,3-Propanediol (PDO), as an important raw material for chemical industry, can be used as an organic solvent in inks, dyeing and printing, coatings, lubricants, or antifreezer industry and the like. 1,3-Propanediol mainly acts as a monomer in the synthesis of polyesters and polyurethane, especially to polymerize with terephthalic acid to form polytrimethylene terephthalate (PTT), which exhibits better performances compared to those polymers synthesized from 1,2-propanediol, butanediol and glycol monomer. Now, tens of million tons polyethylene terephthalates (PET) are consumed every year throughout the world. PTT is comparable to PET in chemical stability, biodegradability, and the like, but more excellent in pollution resistance, toughness, elastic resilience, UV resistance and the like. In addition, PTT also has other advantages, such as abrasion resistance or wearability, low water absorption, low static electricity etc., capable of competing with nylon in carpet market. It also can be used in non-woven fabrics, engineering plastics, clothes, domestic decorates, liner materials, fabrics and the like. PTT was evaluated as one of the top six new petrochemicals in USA in 1998, and considered as the update product instead of PET.

The excellent performance and marketing potential of PTT have been recognized 50 years ago. It is very difficult to produce PTT in a large industrial scale just due to the high technical difficulty and cost in the production of its raw material, 1,3-propanediol. So far, only two international corporations, Dupont and Shell, produce self-used 1,3-propanediol for their PTT synthesis from ethylene oxide or propylene as raw materials via a conventional chemical synthesis route. There are several deficiencies in chemical synthesis processes, including excessive by-products; poor selectivity; requiring special operating conditions, such as high temperature and pressure; enormous equipment costs; its raw materials being non-reproducible resources; and ethylene oxide and the intermediate product acrolein produced in another route being combustible, explosive or virulent hazardous matters, respectively. The fermentation process for producing 1,3-propanediol has been focused in recent years due to the high selectivity and the mild operation conditions.

As a by-product in the 1,3-propanediol fermentation, 2,3-butanediol also is an important raw material in chemical industry. It is a colorless and flavorless liquid, and may be used as fuels, and used to prepare polymers, inks, perfumes, antifreezers, fumigants, humidizers, softening agent, plasticizer, explosives, chiral vehicles for pharmaceuticals and the like. Also, 2,3-butanediol may serve as a very valuable raw material in chemical industry to synthesize other chemicals, for example, dehydrating 2,3-butanediol to form methyl ethyl ketone with quite extensive applications, and further dehydrating to form 1,3-butadiene. 2,3-Butanediol can be polymerized to produce styrene via a Diels-Alder reaction. 2,3-Butanediol and methyl ethyl ketone may condense and then subject to a hydrogenating reaction to form octane, which can be used to produce high quality materials for flight. 2,3-Butanediol reacts with acetic acid to form 2,3-butanediol diacetate, which can be added to butters to improve flavor. Generally, 2,3-butanediol, however, is not be separated and purified as a product due to its low yields in the 1,3-propanediol fermentation.

Presently, there are two major methods for producing 1,3-propanediol, chemical and biological methods. Compared to chemical synthesis methods, microbe fermentation methods for producing 1,3-propanediol possess many significant advantages, including mild production conditions, good selectivity, less by-products, easy to separate and purify, without environmental pollution etc., and more and more attention is thereby paid to such methods.

At present, there are several paths for producing 1,3-propanediol by biological methods:

1. Intestinal bacteria are utilized to convert glycerol to 1,3-propanediol under anaerobic conditions (see, U.S. Pat. No. 5,254,467, EP0373230 A1).

2. Anaerobic fermentation with bacteria such as *Klebsiella* under anaerobic conditions to produce 1,3-propanediol (Ruch et al. Regulation of glycerol catabolism in *Klebsiella aerogenes*. J Bacteriol. 1974, 119(1):50-56; Streekstra et al. Overflow metabolism during anaeric growth of *Klebsiella pneumoniae* NCTC418 on glycerol and dihydroxyacetone in chemostat culture. Arch Microbiol. 1987, 147:268-275; Zeng et al. Pathway analysis of glycerol fermentation by *Klebsiella pneumoniae*: Regulation of reducing equivalent balance and product formation. Enzyme Microbiol Technol. 1993, 15:770-779).

3. *Klebsiella* are utilized under microaerobic conditions to produce 1,3-propanediol by fermentation (see, Wang Jianfang etc., Study on microaerobic conversion of glycerin to 1,3-propanediol by *Klebsiella pneumoniae*, Modern Chemical Industry, 2001, 21(5): 28-31; and Chinese Patent Publication No. CN1348007, a method for microaerobic fermentive production of 1,3-propanediol, issued to Xiu Zhilong etc.).

4. *Klebsiella* are utilized under anaerobic conditions to produce 1,3-propanediol and 2,3-butanediol by fermentation (Biebl et al. Fermentation of glycerol to 1,3-propanediol and 2,3-butanediol. Appl Microbiol Biotechnol, 1998, 50:24-29).

5. 1,3-propanediol and 2,3-butanediol are produced from glycerol by a two-stage microbial fermentation method (Liu Dehua etc., Patent Application No. 200410037692.3).

6. A method for 1,3-propanediol production by a two-step microbial fermentation (Xiu Zhilong etc., Chinese Patent No. ZL01138769.6).

The above methods 1-3 all utilize glycerol as substrates to produce a single product 1,3-propanediol, and the concentration of 1,3-propanediol in broth is very low, so its production costs are very high. Method 4 proposes a fermentation for simultaneously producing 1,3-propanediol and 2,3-butanediol, however, its fermentation level is very low due to the limitations of technical conditions. Method 5 adopts a new process using an anaerobic condition in earlier stage and an aerobic condition in later stage, which significantly increases the concentrations of the fermentation products 1,3-propanediol and 2,3-butanediol, and to some extent, decreases the production costs; but the production costs are still relatively high because this method also utilizes glycerol as substrates. Method 6 provides a two-step fermentation method to produce 1,3-propanediol from raw materials such as starches, which, theoretically, may markedly decrease production costs; but, due to the limitations of technical conditions, the concentration of glycerol is only 49.9 g/L with a yield of only 39.1% by mole, and the 1,3-propanediol concentration is also very low and only 13.18 g/L with a yield of only 22.8% by mole in its most preferred embodiments.

THE DISCLOSURE OF THE INVENTION

One object of the present invention is to provide a method for producing 1,3-propanediol and 2,3-butanediol from raw starch materials.

A method for producing 1,3-propanediol and 2,3-butanediol from raw starch materials provided by the invention includes steps as follows:

1) *Candida krusei* or *Hansenula Arabitolgens* Fang are inoculated into a fermentation medium with the saccharifying liquid of raw starches as a carbon source, using an aerobic condition in earlier stage and an anaerobic condition in later stage, i.e., the yeast cells are cultured on the aerobic condition until glucose-consuming-rate is significantly reduced, and then fermented anaerobically to a glucose concentration of from 5 to 10 g/L. The fermentation broth is collected and filtered to remove the yeast cells in the fermentation broth, and the resultant filtrate is glycerin fermentation broth.

2) *Klebsiella*, *Clostridium butyricum*, or *Clostridium pasteurianum* are inoculated into a fermentation medium in which the glycerin fermentation broth obtained from step 1) serves as a carbon source. The bacteria are fermented anaerobically for 30-32 hours, and then fermented aerobically when the production rate of 1,3-propanediol decreased obviously, and the fermentation was stopped when the concentration of glycerin is reduced to a level below 10 g/L, and finally 1,3-propanediol and 2,3-butanediol are obtained.

Wherein, the yeast cells removed by filtering in the step 1) may be recovered directly for next fermentation batch; the cell recovering may decrease the seed culturing period of the next batch.

The *Candida krusei* or *Hansenula Arabitolgens* Fang are from a primary or secondary seed; the primary seed is prepared according to the following procedures: the *Candida krusei* or *Hansenula Arabitolgens* Fang are inoculated into a seed medium containing the saccharifying liquid of raw starches, and cultured in a shake flask with a liquid load of ⅕ of the flask volume at 30-35° C. for 18-20 hours, using a rotating radius of 25 mm and a rotating speed of from 200 to 250 rpm. The secondary seed is prepared as follows: the primary seed is inoculated into a seed medium with the saccharifying liquid of raw starches as a carbon source in a fermenter, and cultured at 30-35° C. for 5-7 hours, using a mixing speed of from 300 to 500 rpm and an aeration quantity of 0.2-0.5 vvm.

The fermentation medium with the saccharifying liquid of raw starches as a carbon source has a pH of 4-5, and further contains corn slurry and urea; the content of the saccharifying liquid of raw starches is calculated on the basis that all the reducing sugars in the saccharifying liquid of raw starches are considered as glucose, and is up to 260-350 g/L of glucose in the medium; the content of the corn slurry is 2-3 g/L; and the content of urea is 2.5-4 g/L.

The seed medium containing the saccharifying liquid of raw starches has a pH of 4-5, and further contains corn slurry and urea; the content of the saccharifying liquid of raw starches is calculated on the basis that all the reducing sugars in the saccharifying liquid of raw starches are considered as glucose, and is up to 80-100 g/L of glucose in the medium; the content of the corn slurry is 2-3 g/L; and the content of urea is 2-3 g/L.

The raw starches in the step 1) may be starches materials such as sweet potato starch, corn starch, or tapioca; and the DE value of the saccharifying liquid of raw starches is 90-110.

The saccharifying liquid of raw starches may be prepared according to the following procedures: formulating a starch emulsion from raw starches and water in a mass ratio of 1:1800-2000; adding a liquefying enzyme twice at 80-85° C. and 90-95° C. respectively, and for each time, using 3-5 U/gram raw starch; liquefying for 40-50 minutes; then increasing the temperature to 110-120° C. to inactivate the enzyme; cooling; adding a saccharifying enzyme of 150-200 U/gram starch; saccharifying at 50-60° C. for 8-12 hours; and obtaining a saccharifying liquid of raw starches having a DE value of 90-110.

*Klebsiella*, *Clostridium butyricum*, or *Clostridium pasteurianum* are from a primary or secondary seed; the primary seed is prepared according to the following procedures: the *Klebsiella*, *Clostridium butyricum*, or *Clostridium pasteurianum* are inoculated into a seed medium formulated from the glycerin fermentation broth obtained in the step 1), and cultured under aerobic conditions in a shake flask with a liquid load of ⅕ of the flask volume at 30-33° C. for 18-20 hours, using a rotating radius of 25 mm and a rotating speed of from 130 to 150 rpm. The secondary seed is prepared as follows: a primary seed is inoculated into a seed medium formulated from the glycerin fermentation broth obtained in the step 1) in a fermenter, and cultured at 30-33° C. for 5-10 hours, using a mixing speed of from 60 to 150 rpm and an aeration quantity of 0.2-0.5 vvm.

The fermentation medium with the glycerin fermentation broth obtained in the step 1) as a carbon source has a pH of 6.8-8.0, the content of the glycerin fermentation broth is up to 20-80 g/L glycerin in the medium as calculated on a glycerin basis; the fermentation medium with the glycerin fermentation broth as a carbon source further contains 2.225-3.5 g/L $K_2HPO_4 \cdot 3H_2O$, 2.0-4.0 g/L $(NH_4)_2SO_4$, 0.65-1.2 g/L $KH_2PO_4$, 0.1-0.2 g/L $MgSO_4 \cdot 7H_2O$, 1-1.5 g/L yeast powder, a solution of trace elements of 2-3 mL/L, and 0.1 mL/L antifoaming agent. The solution of trace elements is consisting of 70 mg/L $ZnCl_2$, 100 mg/L $MnCl_2 \cdot 4H_2O$, 60 mg/L $H_3BO_3$, 200 mg/L $CoCl_2 \cdot 6H_2O$, 25 mg/L $NiCl_2 \cdot 6H_2O$, 27.64 mg/L $NiCl_2 \cdot H_2O$, 35 mg/L $Na_2MoO_4 \cdot 2H_2O$, 20 mg/L $CuCl_2 \cdot H_2O$, 29.28 mg/L $CuSO_4 \cdot 5H_2O$, and 0.9 mL/L concentrated HCl.

The fermentation medium with the glycerin fermentation broth obtained in the step 1) as a carbon source has a pH of 6.8-8.0, the content of the glycerin fermentation broth is up to 20 g/L glycerin in the medium as calculated on a glycerin basis; the fermentation medium with the glycerin fermentation broth as a carbon source further contains 4.45-5.6 g/L $K_2HPO_4 \cdot 3H_2O$, 2.0-4.0 g/L $(NH_4)_2SO_4$, 1.3-2.6 g/L $KH_2PO_4$, 0.1-0.2 g/L $MgSO_4 \cdot 7H_2O$, 1.0-2.0 g/L yeast powder, 1.0-2.0 g/L $CaCO_3$, and a solution of trace elements of 2-3 mL/L. The solution of trace elements is consisting of 70 mg/L $ZnCl_2$, 100 mg/L $MnCl_2 \cdot 4H_2O$, 60 mg/L $H_3BO_3$, 200 mg/L $CoCl_2 \cdot 6H_2O$, 25 mg/L $NiCl_2 \cdot 6H_2O$, 27.64 mg/L $NiCl_2 \cdot H_2O$, 35 mg/L $Na_2MoO_4 \cdot 2H_2O$, 20 mg/L $CuCl_2 \cdot H_2O$, 29.28 mg/L $CuSO_4 \cdot 5H_2O$, and 0.9 mL/L concentrated HCl.

The fermentation temperature in the fermentation process of the step 1) is 30-35° C.;

The aerobic condition in the step 1) is to aerating air during the fermentation process, with a aeration quantity of 0.5-2 vvm (L/L/min, a ratio of the volume of air aerating into a fermenter per minute to the volume of the fermentation broth in the fermenter); The anaerobic condition in the step 1) is to aerating nitrogen gas during the fermentation process, with a aeration quantity of 0.2-2 vvm (L/L/min, a ratio of the volume of nitrogen gas aerating into a fermenter per minute to the volume of the fermentation broth in the fermenter).

The glycerin fermentation broth obtained in the step 1) is added in fed-batch during the fermentation process of the step 2), allowing the content of glycerin in the medium to maintain at 20-80 g/L.

Nitrogen source is supplemented twice during the fermentation process of the step 2), each adding yeast powder and $(NH_4)_2SO_4$ in an amount of 0.8 g yeast powder/L medium and 1 g $(NH_4)_2SO_4$/L medium, respectively.

The pH is 6.8-8.0 and the fermentation temperature is 30-37° C. during the fermentation process of the step 2).

The method further include a step of purifying 1,3-propanediol and 2,3-butanediol, i.e., collecting the fermentation broth, filtering to remove the bacteria mass, and gathering the filtrate to allow it desalt, distill and rectify under vacuum.

THE PREFERRED EMBODIMENTS TO IMPLEMENT THE INVENTION

The following experimental methods are all conventional methods unless specify otherwise.

Example 1

Producing 1,3-propanediol and 2,3-butanediol from Raw Corn Starches

1. The Liquefying and Saccharifying of the Raw Starch Materials.

1475 g raw corn starches and 2722 L water were formulated as starch emulsion. The emulsion was heated, added liquefying enzyme (5 U/gram starch) twice at 80° C. and 95° C., and liquefied for 50 min. And then the temperature was increased to 110° C. to inactivate the enzyme. The mixture was cooled and added saccharifying enzyme (200 U/gram starch), then saccharified at 60° C. for 9 h. The measured results show that the glucose value (DE (dextrose equivalent) value, referring to the percent of glucose in dry masses, as calculated on the basis that all the reducing sugars in saccharifying liquid are considered as glucoses) of the saccharifying liquid is 103.46 and the dextrose concentration in the saccharifying liquid is 31.55%.

2. Producing Glycerin by the Fermentation of the Saccharifying Liquid (1) Strains: *Candida krusei* 2.1048 (Commercially Available from Institute of Microbiology, Chinese Academy of Sciences)

(2) Media:

Slant medium (g/L): glucose (prepared with the saccharifying liquid of the step 1), 200; corn slurry, 3; urea, 3; and agar, 20.

Seed medium (g/L): glucose (prepared with the saccharifying liquid of the step 1), 100; corn slurry, 3; and urea, 3.

Fermentive medium: glucose (prepared with the saccharifying liquid of the step 1), 315; corn slurry, 3; and urea, 2.5.

The above media are all adjusted to a pH of 4-4.5, and sterilized at 110° C. for 15 min.

(3) Seed Culturing

*Candida krusei* 2.1048 are inoculated into slant medium and cultured at 35° C. for 24 h to activate the strain.

The activated *Candida krusei* 2.1048 are inoculated into seed medium containing saccharifying liquid of raw starch, and primary seeds are obtained through culturing in a shake flask (a 500 mL conical flask, with a liquid loading of 100 mL) at 35° C., 200 rpm (a rotating radius of 25 mm) for 20 hours.

Second seeds are obtained through inoculating the primary seeds into seed medium containing saccharifying liquid of raw starch and culturing at a mixing speed of 300-500 rpm at 35° C. for 5-7 h, with an aeration quantity of 0.2-0.5 vvm.

(4) Fermentation

Fermentation was performed by any one of the following three procedures:

A. Fermentation was performed with a 5 L fermenter and primary seeds. The primary seeds were inoculated into a fermentive medium in a volume ratio of 10% and the fermentation was carried out in the 5 L fermenter, aerating air at a quantity of 2.0 vvm over the first 60 hrs and nitrogen gas at a quantity of 0.5 vvm after 60 hrs at a mixing speed of 500 rpm and culturing for 70 hrs. The fermentation temperature remained at 30° C. throughout the fermentation process. The glycerin yield was measured and the results showed that glycerin was at a concentration of 165 g/L, the remaining sugars were at a concentration of 5 g/L, and the yield of glycerin vs. glucose was 52.4% by mass.

B. Fermentation was performed with a 500 L fermenter and secondary seeds. The secondary seeds were inoculated into a fermentive medium in a volume ratio of 10% and the fermentation was carried out in the 500 L fermenter, aerating air at a quantity of 0.8 vvm over the first 60 hrs and nitrogen gas at a quantity of 0.2 vvm after 60 hrs at a mixing speed of 300 rpm and culturing for 72 hrs. The fermentation temperature remained at 33° C. throughout the fermentation process. The glycerin yield was measured and the results showed that glycerin was at a concentration of 179 g/L, the remaining sugars were at a concentration of 5 g/L, and the yield of glycerin vs. glucose was 55.38% by mass.

C. Fermentation was performed with a 75000 L fermenter and secondary seeds. The secondary seeds were inoculated into a fermentive medium in a volume ratio of 10% and the fermentation was carried out in the 75000 L fermenter, aerating air at a quantity of 0.5 vvm over the first 60 hrs and nitrogen gas at a quantity of 0.2 vvm after 60 hrs at a mixing speed of 300 rpm and culturing for 72 hrs. The fermentation temperature remained at 35° C. throughout the fermentation process. The glycerin yield was measured and the results showed that glycerin was at a concentration of 158 g/L, the remaining sugars were at a concentration of 5 g/L, and the yield of glycerin vs. glucose was 53.3% by mass.

3. Producing 1,3-propanediol and 2,3-butanediol by the Fermentation of the Glycerin Fermentation Broth (1) The glycerin fermentation broth of the previous step was filtered to remove *Candida krusei* 2.1048. The filtered cells were used directly in the next batch of glycerin fermentation under the same fermentation conditions with the first batch. The resultant filtrate are used to ferment 1,3-propanediol and 2,3-butanediol.

(2) Strains: *Klebsiella pneumoniae* 1.1734 (commercially available from Institute of Microbiology, Chinese Academy of Sciences)

(3) The ingredients of seed and fermentation media for 1,3-propanediol are listed in Table 1 below, in which the compositions of the solution of trace elements are listed in Table 2 below.

TABLE 1

The ingredients of seed and fermentation media

| Ingredients of Medium | Seed Medium (/L) | Fermentation medium (/L) |
|---|---|---|
| Glycerin (formulated by the glycerin fermentation broth of step 2) | 20 g | 20-80 g |
| $K_2HPO_4 \cdot 3H_2O$ | 4.45 g | 2.225 g |
| $(NH_4)_2SO_4$ | 2.0 g | 2.0 g |
| $KH_2PO_4$ | 1.3 g | 0.65 g |
| $MgSO_4 \cdot 7H_2O$ | 0.2 g | 0.2 g |
| Yeast Powder | 1.0 g | 1.5 g |
| Trace elements solution | 2 mL | 2 mL |
| $CaCO_3$ | 2.0 g | |
| Anti-foam agents | | 0.1 mL |

TABLE 2

Ingredients of Trace Elements Solution
Trace elements solution (mg/L)

| | |
|---|---|
| $ZnCl_2$ | 70 (mg/L) |
| $MnCl_2 \cdot 4H_2O$ | 100 (mg/L) |
| $H_3BO_3$ | 60 (mg/L) |
| $CoCl_2 \cdot 6H_2O$ | 200 (mg/L) |
| $NiCl_2 \cdot 6H_2O$ | 25 (mg/L) |
| $NiCl_2 \cdot H_2O$ | 27.64 (mg/L) |
| $Na_2MoO_4 \cdot 2H_2O$ | 35 (mg/L) |
| $CuCl_2 \cdot H_2O$ | 20 (mg/L) |
| $CuSO_4 \cdot 5H_2O$ | 29.28 (mg/L) |
| Concentrated HCl (37%) | 0.9 (mL/L) |

The pH of the media above is 6.8-8.0.

(4) Seed culturing: *Klebsiella pneumoniae* 1.1734 was inoculated into the seed medium formulated with the glycerin fermentation broth of step 2 (a 500 mL conical flask with a liquid loading of 100 mL) and cultured at 30° C. at a shaker speed of 150 rpm (with a rotating radius of 25 mm). Primary seeds were obtained by an aerobic culture for 18 hrs; and then the fermentation broth in this shaking flask was inoculated in a volume ratio of 2% into the fermenter loaded with the seed medium and cultured at a mixing speed of 60-150 rpm at 30° C. with an aeration quantity of 0.2-0.5 vvm for 5-10 hours to obtain secondary seeds.

(5) Fermentation Culturing:

Fermentation was performed by any one of the following methods C, D and E, and methods A and B were taken as controls:

A. A 5 L fermenter was used, culturing temperature was at 37° C., and the pH value was adjusted to 6.8 with KOH. The seed liquid was inoculated into the fermentation medium (with a glycerin concentration of 50 g/L) prepared with the glycerin fermentation broth of step 2, no glycerin fermentation broth was feed during the fermentation process. The fermenter was rotated at a speed of 150 rpm. Nitrogen gas was aerated at 0.5 vvm. The fermentation was carried out for 30 hrs, and the concentrations of 1,3-propanediol and 2,3-butanediol were 21 g/L and 2 g/L, respectively.

B. A 5 L fermenter was used, culturing temperature was at 37° C., and the pH value was adjusted to 6.8 with KOH. The seed liquid was inoculated into the fermentation medium (with a glycerin concentration of 80 g/L) prepared with the glycerin fermentation broth of step 2, no glycerin fermentation broth was feed during the fermentation process. The fermenter was rotated at a speed of 150 rpm. The air was aerated at 0.5 vvm. The fermentation was carried out for 30 hrs, and the concentrations of 1,3-propanediol and 2,3-butanediol were 35 g/L and 6.6 g/L, respectively.

C. A 5 L fermenter was used, culturing temperature was at 37° C., and the pH value was adjusted to 6.8 with KOH. The seed liquid was inoculated into the fermentation medium (with a glycerin concentration of 30 g/L) prepared with the glycerin fermentation broth of step 2, with adding the glycerin fermentation broth in a fed-batch way during the fermentation process and controlling its flow rate to remain the glycerin concentration at 30 g/L. The fermenter was rotated at a speed of 150 rpm. Nitrogen gas was first aerated and air aerated after 32 hours, both at 0.5 vvm. Nutrition was supplemented twice at 16 h and 30 h during the fermentation process (each adding yeast powder and $(NH_4)_2SO_4$ in an amount of 0.8 g yeast powder/L medium and 1 g $(NH_4)_2SO_4$/L medium, respectively). The fermentation was completed after 64 h. The fermentation broth was collected, filtered to remove the strains, and the resultant filter liquor was collected to desalt, distill and rectify under vacuum to obtain products, 1,3-propanediol and 2,3-butanediol. The measured results showed that at the completion of the fermentation, the concentrations of 1,3-propanediol and 2,3-butanediol in the fermentation broth were 70 g/L and 16 g/L, respectively, and the yield of 1,3-propanediol was 51% by mole (the ratio of the moles of 1,3-propanediol to the moles of the glycerin consumed), the yield of the total diols was 71.85% by mole (the ratio of the moles of 1,3-propanediol and 2,3-butanediol to the moles of the glycerin consumed).

D. A 500 L fermenter was used. 50 L secondary seed liquid was inoculated into the fermentation medium (with a glycerin concentration of 30 g/L) prepared with the glycerin fermentation broth of step 2, with the fermenter rotating at a speed of 60 rpm and using an aeration quantity of 0.3 vvm. The glycerin fermentation broth was added in a fed-batch way during the fermentation process and controlling its flow rate to remain the glycerin concentration at 30 g/L. The other conditions were the same as those for a 5 L fed-batch fermentation. At the completion of the fermentation, the concentrations of 1,3-propanediol and 2,3-butanediol in the fermentation broth were 72 g/L and 25.4 g/L, respectively, the yield of 1,3-propanediol was 55.38% by mole, and the yield of the total diols was 71.85% by mole.

E. A 5000 L fermenter was used. 500 L secondary seed liquid was inoculated into the initial fermentation medium (with a glycerin concentration of 30 g/L) prepared with the glycerin fermentation broth described above. The glycerin fermentation broth was added in a fed-batch way during the fermentation process and controlling its flow rate to remain the glycerin concentration at 30 g/L. The fermentation conditions were the same as those for a 500 L fermenter. At the completion of the fermentation, the concentrations of 1,3-propanediol and 2,3-butanediol in the fermentation broth were 66.6 g/L and 30.4 g/L, respectively, and the yield of 1,3-propanediol was 59.1% by mole, the yield of the total diols was 83.2% by mole.

4. Cell recycle: the resultant cells were filtered off from the glycerin fermentation broth for direct use in the next batch of glycerin fermentation. And the fermentation conditions were all the same as the first batch. The cell viability substantially remained unchanged for at least 10 recycles, and the glycerin concentration remained stable.

Example 2

Producing 1,3-propanediol and 2,3-butanediol from Raw Sweet Potato Starches

1. The Liquefying and Saccharifying of the Raw Starch Materials.

1475 g raw sweet potato starches and 2722 L water were formulated as starch emulsion. The emulsion was heated, added liquefying enzyme (5 U/gram starch) twice at 80° C. and 95° C., and liquefied for 50 min. And then the temperature was increased to 110° C. to inactivate the enzyme. The mixture was cooled and added saccharifying enzyme (200 U/gram starch), then saccharified at 60° C. for 9 h. The measured results show that the glucose value (DE (dextrose equivalent) value, referring to the percent of glucose in dry masses, as calculated on the basis that all the reducing sugars in saccharifying liquid are considered as glucoses) of the saccharifying liquid is 95.5 and the dextrose concentration in the saccharifying liquid is 26.8%.

2. Producing Glycerin by the Fermentation of the Saccharifying Liquid (1) Strains:

*Hansenula Arabitolgens* Fang 2.887, commercially available from Institute of Microbiology, Chinese Academy of Sciences (2) Media:

Slant medium (g/L): glucose (prepared with the saccharifying liquid of the step 1), 200; corn slurry, 2; and agar, 20.

Seed medium (g/L): glucose (prepared with the saccharifying liquid of the step 1), 100; corn slurry, 2; and urea, 2.

Fermentive medium (g/L): glucose (prepared with the saccharifying liquid of the step 1), 268; corn slurry, 2; and urea, 4.

The above media are all adjusted to a pH of 4-4.5, and sterilized at 110° C. for 15 min.

(3) Seed Culturing

*Hansenula Arabitolgens* Fang 2.887 are inoculated into slant medium and cultured at 35° C. for 24 h to activate the strain.

The activated *Hansenula Arabitolgens* Fang 2.887 are inoculated into seed medium containing saccharifying liquid of raw starch, and primary seeds are obtained through culturing in a shake flask (a 500 mL conical flask, with a liquid loading of 100 mL) at 30° C., 200 rpm (a rotating radius of 25 mm) for 20 hours.

Second seeds are obtained through inoculating the primary seeds into seed medium containing saccharifying liquid of raw starch and culturing at a mixing speed of 300-500 rpm at 30° C. for 5-7 h, with an aeration quantity of 0.2-0.5 vvm.

(4) Fermentation

Fermentation was performed by any one of the following three procedures A, B, C:

A. Fermentation was performed with a 5 L fermenter and primary seeds. The primary seeds were inoculated into a fermentive medium in a volume ratio of 10% and fermented in the 5 L fermenter, aerating air at a quantity of 2.0 vvm over the first 60 hrs and nitrogen gas at a quantity of 0.5 vvm after 60 hrs at a mixing speed of 500 rpm and culturing for 70 hrs. The fermentation temperature remained at 30° C. throughout the fermentation process. The glycerin yield was measured and the results showed that glycerin was at a concentration of 140 g/L, the remaining sugars were at a concentration of 4.8 g/L, and the yield of glycerin vs. glucose was 53% by mass.

B. Fermentation was performed with a 500 L fermenter and secondary seeds. The secondary seeds were inoculated into a fermentive medium in a volume ratio of 10% and fermented in the 500 L fermenter, aerating air at a quantity of 0.8 vvm over the first 60 hrs and nitrogen gas at a quantity of 0.2 vvm after 60 hrs at a mixing speed of 300 rpm and culturing for 72 hrs. The fermentation temperature remained at 33° C. throughout the fermentation process. The glycerin yield was measured and the results showed that glycerin was at a concentration of 146 g/L, the remaining sugars were at a concentration of 4.7 g/L, and the yield of glycerin vs. glucose was 55.7% by mass.

C. Fermentation was performed with a 75000 L fermenter and secondary seeds. The secondary seeds were inoculated into a fermentive medium in a volume ratio of 10% and fermented in the 75000 L fermenter, aerating air at a quantity of 0.5 vvm over the first 60 hrs and nitrogen gas at a quantity of 0.2 vvm after 60 hrs at a mixing speed of 300 rpm and culturing for 72 hrs. The fermentation temperature remained at 35° C. throughout the fermentation process. The glycerin yield was measured and the results showed that glycerin was at a concentration of 142 g/L, the remaining sugars were at a concentration of 4 g/L, and the yield of glycerin vs. glucose was 54.1% by mass.

3. Producing 1,3-propanediol and 2,3-butanediol by the Fermentation of the Glycerin Fermentation Broth (1) The glycerin fermentation broth of the previous step was filtered to remove *Hansenula Arabitolgens* Fang 2.887 cells. The filtered cells were used directly in next batch of glycerin fermentation under the same fermentation conditions with the first batch. The resultant filtrate are used to ferment 1,3-propanediol and 2,3-butanediol.

(2) Strains: *Clostridium pasteurianum* 1.208, commercially available from Institute of Microbiology, Chinese Academy of Sciences.

(3) The ingredients of seed and fermentation media for 1,3-propanediol are listed in Table 1 below, in which the compositions of trace element solutions are listed in Table 2 below.

TABLE 1

The ingredients for seed and fermentation media

| Ingredients of Medium | Seed Medium (/L) | Fermentation medium (/L) |
|---|---|---|
| Glycerin (formulated by the glycerin fermentation broth of step 2) | 20 g | 20-80 g |
| $K_2HPO_4 \cdot 3H_2O$ | 4.45 g | 2.225 g |
| $(NH_4)_2SO_4$ | 2.0 g | 2.0 g |
| $KH_2PO_4$ | 1.3 g | 0.65 g |
| $MgSO_4 \cdot 7H_2O$ | 0.2 g | 0.2 g |
| Yeast Powder | 1.0 g | 1.5 g |
| Trace elements solution | 2 mL | 2 mL |
| $CaCO_3$ | 2.0 g | |
| Anti-foam agents | | 0.1 mL |

TABLE 2

Ingredients of Trace Elements Solution
Trace elements solution (mg/L)

| | |
|---|---|
| $ZnCl_2$ | 70 (mg/L) |
| $MnCl_2 \cdot 4H_2O$ | 100 (mg/L) |
| $H_3BO_3$ | 60 (mg/L) |
| $CoCl_2 \cdot 6H_2O$ | 200 (mg/L) |
| $NiCl_2 \cdot 6H_2O$ | 25 (mg/L) |
| $NiCl_2 \cdot H_2O$ | 27.64 (mg/L) |
| $Na_2MoO_4 \cdot 2H_2O$ | 35 (mg/L) |
| $CuCl_2 \cdot H_2O$ | 20 (mg/L) |

TABLE 2-continued

Ingredients of Trace Elements Solution
Trace elements solution (mg/L)

| | |
|---|---|
| $CuSO_4 \cdot 5H_2O$ | 29.28 (mg/L) |
| Concentrated HCl (37%) | 0.9 (mL/L) |

The pH of the media above is 6.8-8.0.

(4) Seed culturing:

*Clostridium pasteurianum* 1.208 was inoculated into the seed medium formulated with the glycerin fermentation broth of step 2 (a 500 mL conical flask with a liquid loading of 100 mL) and cultured at 33° C. at a shaker speed of 130 rpm (with a rotating radius of 25 mm). Primary seeds were obtained by an aerobic culture for 18 hrs; and then the fermentation broth in this shaking flask was inoculated in a volume ratio of 2% into the fermenter loaded with the seed medium and cultured at a mixing speed of 60-150 rpm at 33° C. with an aeration quantity of 0.2-0.5 vvm for 5-10 hours to obtain secondary seeds.

(5) Fermentation Culturing:

Fermentation was performed by any one of the following methods C, D and E, and methods A and B were taken as controls:

A. A 5 L fermenter was used, culturing temperature was at 37° C., and the pH value was adjusted to 6.8 with KOH. The seed liquid was inoculated into the fermentation medium (with a glycerin concentration of 50 g/L) prepared with the glycerin fermentation broth of step 2, no glycerin fermentation broth was feed during the fermentation process. The fermenter was rotated at a speed of 150 rpm. Nitrogen gas was aerated at 0.5 vvm. The fermentation was carried out for 30 hrs, and the concentrations of 1,3-propanediol and 2,3-butanediol were 24 g/L and 1.7 g/L, respectively.

B. A 5 L fermenter was used, culturing temperature was at 37° C., and the pH value was adjusted to 6.8 with KOH. The seed liquid was inoculated into the fermentation medium (with a glycerin concentration of 80 g/L) prepared with the glycerin fermentation broth of step 2, no glycerin fermentation broth was feed during the fermentation process. The fermenter was rotated at a speed of 150 rpm. The air was aerated at 0.5 vvm. The fermentation was carried out for 30 hrs, and the concentrations of 1,3-propanediol and 2,3-butanediol were 38 g/L and 5.6 g/L, respectively.

C. A 5 L fermenter was used, culturing temperature was at 37° C., and the pH value was adjusted to 6.8 with KOH. The seed liquid was inoculated into the fermentation medium (with a glycerin concentration of 30 g/L) prepared with the glycerin fermentation broth of step 2, with adding the glycerin fermentation broth in a fed-batch way during the fermentation process and controlling its flow rate to remain the glycerin concentration at 30 g/L. The fermenter was rotated at a speed of 150 rpm. Nitrogen gas was first aerated and air aerated after 32 hours, both at 0.5 vvm. Nutrition was supplemented twice at 16 h and 30 h during the fermentation process (each adding yeast powder and $(NH_4)_2SO_4$ in an amount of 0.8 g yeast powder/L medium and 1 g $(NH_4)_2SO_4$/L medium, respectively). The fermentation was completed at 64 h. The fermentation broth was collected, filtered to remove the strains, and the resultant filtrate was collected to desalt, distill and rectify under vacuum to obtain products, 1,3-propanediol and 2,3-butanediol. The measured results showed that at the completion of the fermentation, the concentrations of 1,3-propanediol and 2,3-butanediol in the fermentation broth were 50 g/L and 18 g/L, respectively, and the yield for 1,3-propanediol was 54% by mole (the ratio of the moles of 1,3-propanediol to the moles of the glycerin consumed), the yield for the total diols was 70% by mole (the ratio of the moles of 1,3-propanediol and 2,3-butanediol to the moles of the glycerin consumed).

D. A 500 L fermenter was used. 50 L secondary seed liquid was inoculated into the fermentation medium (with a glycerin concentration of 30 g/L) prepared with the glycerin fermentation broth of step 2, with the fermenter rotating at a speed of 60 rpm and using an aeration quantity of 0.3 vvm. The glycerin fermentation broth was added in a fed-batch way during the fermentation process and controlling its flow rate to remain the glycerin concentration at 30 g/L. The other conditions were the same as those for a 5 L fed-batch fermentation. At the completion of the fermentation, the concentrations of 1,3-propanediol and 2,3-butanediol in the fermentation broth were 54 g/L and 22 g/L, respectively, and the yield for 1,3-propanediol was 55% by mole, the yield for the total diols was 73% by mole.

E. A 5000 L fermentater was used. 500 L secondary seed liquid was inoculated into the initial fermentation medium (with a glycerin concentration of 30 g/L) prepared with the glycerin fermentation broth described above. The glycerin fermentation broth was added in a fed-batch way during the fermentation process and controlling its flow rate to remain the glycerin concentration at 30 g/L. The fermentation conditions were the same as those for a 500 L fermenter. At the completion of the fermentation, the concentrations of 1,3-propanediol and 2,3-butanediol in the fermentation broth were 57.6 g/L and 27.3 g/L, respectively, and the yield for 1,3-propanediol was 56% by mole, the yield for the total diols was 76.2% by mole.

4. Cell recycle: the resultant cells were filtered off from the glycerin fermentation broth for direct use in next batch of glycerin fermentation. And the fermentation conditions were all the same as the first batch. The cell viability substantially remained unchanged for at least 10 recycles, and the glycerin concentration remained stable.

INDUSTRIAL APPLICATIONS

The experiments show that, the methods of the present invention can significantly increase the concentration and yield of glycerin and 1,3-propanediol during the production of 1,3-propanediol by a two-step fermentation method, while obtaining 1,3-propanediol and 2,3-butanediol with high added value, thus effectively increasing the availability ratio of raw materials and reducing the production cost. The present method achieves good effects when applied to 5 L, 500 L and 5000 L fermenter, in which the glycerin concentration obtained by fermentation is up to 158-179 g/L, the 1,3-propanediol concentration obtained by fermentation is up to 66-72 g/L, and 2,3-butanediol concentration is up to 16-30.4 g/L.

What is claimed is:
1. A method for producing 1,3-propanediol and 2,3-butanediol from raw starch materials, including the following steps:
   1) inoculating *Candida krusei* or *Hansenula Arabitolgens* Fang into a fermentation medium with the saccharifying liquid of the raw starches as a carbon source; culturing in an aerobic condition until glucose-consuming-rate is significantly reduced, and then fermenting anaerobically to a glucose concentration of 4 to 10 g/L; collecting and filtering the fermentation broth to remove the yeast cells in the fermentation broth, thereby obtaining the resultant filtrate as glycerin fermentation broth;

2) inoculating *Klebsiella, Clostridium butyricum*, or *Clostridium pasteurianum* into a fermentation medium in which the glycerin fermentation broth obtained from step 1) serves as a carbon source; fermenting the bacteria anaerobically for 30-32 hours, and then fermenting aerobically when the production rate of 1,3-propanediol decreased obviously, and stopping the fermentation when the concentration of glycerin is reduced to a level below 10 g/L, thereby obtaining 1,3-propanediol and 2,3-butanediol.

2. The method of claim 1, wherein the yeast cells removed by filtering in the step 1) are recovered directly for next batch of fermentation.

3. The method of claim 1, wherein the *Candida krusei* or *Hansenula Arabitolgens* Fang is from a primary or secondary seed; wherein the primary seed is prepared according to the following steps: inoculating the *Candida krusei* or *Hansenula Arabitolgens* Fang into a seed medium containing the saccharifying liquid of raw starches, culturing in a shake flask with a liquid load of ⅕ of the flask volume at 30-35° C. for 20 hours, using a rotating radius of 25 mm and a rotating speed of from 200 to 250 rpm; and the secondary seed is prepared as follows: inoculating a primary seed into a seed medium with the saccharifying liquid of raw starches as a carbon source in a fermenter, and culturing at 30-35° C. for 5-7 hours, using a mixing speed of from 300 to 500 rpm and an aeration quantity of 0.2-0.5 vvm.

4. The method of claim 1, wherein the fermentation medium with the saccharifying liquid of raw starches as a carbon source has a pH of 4-5, and further contains corn slurry and urea; the content of the saccharifying liquid of raw starches is calculated on the basis that all the reducing sugars in the saccharifying liquid of raw starches are considered as glucose, and is up to 260-350 g/L of glucose in the medium; the content of the corn slurry is 2-3 g/L; and the content of the urea is 2.5-4 g/L.

5. The method of claim 3, wherein the seed medium containing the saccharifying liquid of raw starches has a pH of 4-5, and further contains corn slurry and urea; the content of the saccharifying liquid of raw starches is calculated on the basis that all the reducing sugars in the saccharifying liquid of raw starches are considered as glucose, and is up to 80-100 g/L of glucose in the medium; the content of the corn slurry is 2-3 g/L; and the content of the urea is 2-3 g/L.

6. The method of claim 1, wherein *Klebsiella, Clostridium butyricum*, or *Clostridium pasteurianum* are from a primary or secondary seed; the primary seed is prepared according to the following steps: inoculating the *Klebsiella, Clostridium butyricum*, or *Clostridium pasteurianum* into a seed medium formulated from the glycerin fermentation broth obtained in the step 1), and culturing under aerobic conditions in a shake flask with a liquid load of ⅕ of the flask volume at 30-33° C. for 18-20 hours, using a rotating radius of 25 mm and a rotating speed of from 130 to 150 rpm, to obtain the primary seed; and the secondary seed is prepared by inoculating: a primary seed into a seed medium formulated from the glycerin fermentation broth obtained in the step 1) in a fermenter, and culturing at 30-33° C. for 5-10 hours, using a mixing speed of from 60 to 150 rpm and an aeration quantity of 0.2-0.5 vvm, to obtain the secondary seed.

7. The method of claim 1, wherein the fermentation medium with the glycerin fermentation broth obtained in the step 1) as a carbon source has a pH of 6.8-8.0, the content of the glycerin fermentation broth is up to 20-80 g/L glycerin in the medium as calculated on a glycerin basis; the fermentation medium with the glycerin fermentation broth as a carbon source further contains 2.225-3.5 g/L $K_2HPO_4.3H_2O$, 2.0-4.0 g/L $(NH_4)_2SO_4$, 0.65-1.2 g/L $KH_2PO_4$, 0.1-0.2 g/L $MgSO_4.7H_2O$, 1-1.5 g/L yeast powder, a solution of trace elements of 2-3 mL/L, and 0.1 mL/L antifoaming agent; the solution of trace elements is consisting of 70 mg/L $ZnCl_2$, 100 mg/L $MnCl_2.4H_2O$, 60 mg/L $H_3BO_3$, 200 mg/L $CoCl_2.6H_2O$, 25 mg/L $NiCl_2.6H_2O$, 27.64 mg/L $NiCl_2.H_2O$, 35 mg/L $Na_2MoO_4.2H_2O$, 20 mg/L $CuCl_2.H_2O$, 29.28 mg/L $CuSO_4.5H_2O$, and 0.9 mL/L concentrated HCl.

8. The method of claim 6, wherein the fermentation medium with the glycerin fermentation broth obtained in the step 1) as a carbon source has a pH of 6.8-8.0, the content of the glycerin fermentation broth is up to 20-25 g/L glycerin in the medium as calculated on a glycerin basis; the fermentation medium with the glycerin fermentation broth as a carbon source further contains 4.45-5.6 g/L $K_2HPO_4.3H_2O$, 2.0-4.0 g/L $(NH_4)_2SO_4$, 1.3-2.6 g/L $KH_2PO_4$, 0.1-0.2 g/L $MgSO_4.7H_2O$, 1.0-2.0 g/L yeast powder, 1.0-2.0 g/L $CaCO_3$, and a solution of trace elements of 2-3 mL/L; the solution of trace elements is consisting of 70 mg/L $ZnCl_2$, 100 mg/L $MnCl_2.4H_2O$, 60 mg/L $H_3BO_3$, 200 mg/L $CoCl_2.6H_2O$, 25 mg/L $NiCl_2.6H_2O$, 27.64 mg/L $NiCl_2.H_2O$, 35 mg/L $Na_2MoO_4.2H_2O$, 20 mg/L $CuCl_2.H_2O$, 29.28 mg/L $CuSO_4.5H_2O$, and 0.9 mL/L concentrated HCl.

9. The method of claim 1, wherein the raw starches in the step 1) are sweet potato starch, corn starch, or tapioca; and the DE value of the saccharifying liquid of raw starches is 90-110.

10. The method of claim 9, wherein the saccharifying liquid of raw starches is prepared according to the following procedures:

formulating the raw starches and water in a mass ratio of 1:1800-2000 to obtain a starch emulsion;

adding a liquefying enzyme twice at 80-85° and 90-95° respectively, each 3-5 U/gram raw starch;

liquefying for 40-50 minutes;

then increasing the temperature to 110-120° to inactivate the enzyme;

cooling;

adding a saccharifying enzyme of 150-200 U/gram starch;

saccharifying at 50-60° for 8-12 hours; and obtaining a saccharifying liquid of raw starches having a DE value of 100-110.

11. The method of claim 1, wherein the fermentation temperature in the fermentation process of the step 1) is 30-35°; the aerobic condition in the step 1) is aerating air during the fermentation process, with a aeration quantity of 0.5-2 vvm; and the anaerobic condition in the step 1) is aerating nitrogen gas during the fermentation process, with a aeration quantity of 0.2-2 vvm.

12. The method of claim 1, wherein the glycerin fermentation broth obtained in the step 1) is added in fed-batch during the fermentation process of the step 2), allowing the content of glycerin in the medium to maintain at 20-80 g/L.

13. The method of claim 1, wherein nutrition is supplemented twice during the fermentation process of the step 2), each adding yeast powder and $(NH_4)_2SO_4$ in an amount of 0.8 g yeast powder/L medium and 1 g $(NH_4)_2SO_4$/L medium, respectively.

14. The method of claim 1, wherein the pH is 6.8-8.0 and the fermentation temperature is 30-37° during the fermentation process of the step 2); the anaerobic condition in the step 2) is aerating nitrogen gas during the fermentation process, with an aeration quantity of 0.1-0.5 vvm; and the aerobic condition in the step 2) is aerating air during the fermentation process, with an aeration quantity of 0.1-0.5 vvm.

15. The method of claim 1, further including a step of purifying 1,3-propanediol and 2,3-butanediol, by collecting the fermentation broth, filtering to remove the bacteria, and gathering the filtrate to desalt, distill and rectify under vacuum.

* * * * *

UNITED STATES PATENT AND TRADEMARK OFFICE
CERTIFICATE OF CORRECTION

| | | |
|---|---|---|
| PATENT NO. | : 7,968,319 B2 | Page 1 of 1 |
| APPLICATION NO. | : 11/917682 | |
| DATED | : June 28, 2011 | |
| INVENTOR(S) | : Liu et al. | |

It is certified that error appears in the above-identified patent and that said Letters Patent is hereby corrected as shown below:

At column 2, line 31, please delete "anaeric" and insert therefore, --anaerobic--.

At column 12, line 21, please delete "fermentater" and insert therefore, --fermenter--.

At column 13, line 59, please delete "inoculating:" and insert therefore, --inoculating--.

Signed and Sealed this
Twenty-eighth Day of February, 2012

David J. Kappos
*Director of the United States Patent and Trademark Office*